(12) United States Patent
Han (10) Patent No.: US 9,279,125 B2
(45) Date of Patent: Mar. 8, 2016

(54) ANTI-INFLUENZA NUCLEIC ACID, PEPTIDE NUCLEIC ACID AND PREPARATIONS THEREOF

(71) Applicant: NANJING SEN NAN BIOTECHNOLOGY RESEARCH CO., LTD, Xuanwu Borough, Nanjing, Jiangsu (CN)

(72) Inventor: Jianbao Han, Nanjing (CN)

(73) Assignee: NANJING SEN NAN BIOTECHNOLOGY RESEARCH CO., LTD., Nanjing, Jiangsu (CN)

( * ) Notice: Subject to any disclaimer, the term of this patent is extended or adjusted under 35 U.S.C. 154(b) by 0 days.

(21) Appl. No.: 14/348,950

(22) PCT Filed: Oct. 9, 2012

(86) PCT No.: PCT/CN2012/082615
§ 371 (c)(1),
(2) Date: Apr. 1, 2014

(87) PCT Pub. No.: WO2013/067873
PCT Pub. Date: May 16, 2013

(65) Prior Publication Data
US 2014/0329763 A1   Nov. 6, 2014

(30) Foreign Application Priority Data

Nov. 9, 2011   (CN) .......................... 2011 1 0351833

(51) Int. Cl.
*C12N 15/113*   (2010.01)
*C07K 14/00*   (2006.01)

(52) U.S. Cl.
CPC ............ *C12N 15/1131* (2013.01); *C07K 14/00* (2013.01); *C12N 2310/11* (2013.01); *C12N 2310/3181* (2013.01)

(58) Field of Classification Search
None
See application file for complete search history.

(56) References Cited

U.S. PATENT DOCUMENTS

| | | | |
|---|---|---|---|
| 8,481,506 B2 * | 7/2013 | Bentwich et al. ........... | 514/44 A |
| 2007/0213293 A1 * | 9/2007 | McSwiggen et al. ........... | 514/44 |
| 2008/0248461 A1 * | 10/2008 | Park et al. .......................... | 435/5 |
| 2011/0097707 A1 | 4/2011 | Manoharan et al. | |
| 2011/0236417 A1 | 9/2011 | Watanabe et al. | |
| 2013/0296181 A1 * | 11/2013 | Tyler ................................. | 506/9 |

FOREIGN PATENT DOCUMENTS

WO    WO2012009813 A1 *   1/2012

* cited by examiner

*Primary Examiner* — Tracy Vivlemore
(74) *Attorney, Agent, or Firm* — Nath, Goldberg & Meyer; Tanya E. Harkins; Joshua B. Goldberg (57) ABSTRACT

Disclosed are an anti-influenza nucleic acid, peptide nucleic acid and preparations thereof. The nucleic acid of the invention consists of any one or several of SEQ ID NOs: 1-12, and any one or several of SEQ ID NOs: 13-24. The peptide nucleic acid of the invention consists of any one or several of SEQ ID NOs: 25-36, and any one or several of SEQ ID NOs: 37-48. The peptide nucleic acid preparation of the invention has effective ingredients of said peptide nucleic acids. The anti-influenza peptide nucleic acid of the invention is of high bioavailability and stable physical and chemical properties with no toxic or side effect and no drug tolerance. With low cost, the drugs can inhibit influenza virus replication and have good anti-virus effect.

8 Claims, 2 Drawing Sheets

SEQUENCE LISTING

```
<160> NUMBER OF SEQ ID NOS: 48

<210> SEQ ID NO 1
<211> LENGTH: 23
<212> TYPE: RNA
<213> ORGANISM: artificial sequence
<220> FEATURE:
<223> OTHER INFORMATION: synthesized oligonucleotide

<400> SEQUENCE: 1
```

-continued gguauucuuu ccagcaaaua cau                              23

<210> SEQ ID NO 2
<211> LENGTH: 23
<212> TYPE: RNA
<213> ORGANISM: artificial sequence
<220> FEATURE:
<223> OTHER INFORMATION: synthesized oligonucleotide

<400> SEQUENCE: 2
aauguuaucu cccucuuaag cuu                              23

<210> SEQ ID NO 3
<211> LENGTH: 23
<212> TYPE: RNA
<213> ORGANISM: artificial sequence
<220> FEATURE:
<223> OTHER INFORMATION: synthesized oligonucleotide

<400> SEQUENCE: 3
caugucuuau uaauggauua guu                              23

<210> SEQ ID NO 4
<211> LENGTH: 23
<212> TYPE: RNA
<213> ORGANISM: artificial sequence
<220> FEATURE:
<223> OTHER INFORMATION: synthesized oligonucleotide

<400> SEQUENCE: 4
cgaucaauaa uccacaauau cag                              23

<210> SEQ ID NO 5
<211> LENGTH: 23
<212> TYPE: RNA
<213> ORGANISM: artificial sequence
<220> FEATURE:
<223> OTHER INFORMATION: synthesized oligonucleotide

<400> SEQUENCE: 5
ucuucuuugu cauaaaggau gag                              23

<210> SEQ ID NO 6
<211> LENGTH: 23
<212> TYPE: RNA
<213> ORGANISM: artificial sequence
<220> FEATURE:
<223> OTHER INFORMATION: synthesized oligonucleotide

<400> SEQUENCE: 6
ugauuaacuc cauugcuauu guu                              23

<210> SEQ ID NO 7
<211> LENGTH: 22
<212> TYPE: RNA
<213> ORGANISM: artificial sequence
<220> FEATURE:
<223> OTHER INFORMATION: synthesized oligonucleotide

<400> SEQUENCE: 7
cuuacuugau ccaucauugc cc                               22

<210> SEQ ID NO 8
<211> LENGTH: 22
<212> TYPE: RNA
<213> ORGANISM: artificial sequence

```
<220> FEATURE:
<223> OTHER INFORMATION: synthesized oligonucleotide

<400> SEQUENCE: 8
cauucucauu ugaagcaauc ug                                              22

<210> SEQ ID NO 9
<211> LENGTH: 22
<212> TYPE: RNA
<213> ORGANISM: artificial sequence
<220> FEATURE:
<223> OTHER INFORMATION: synthesized oligonucleotide

<400> SEQUENCE: 9 gcuucuuuc uucucuuug uu                                                22

<210> SEQ ID NO 10
<211> LENGTH: 22
<212> TYPE: RNA
<213> ORGANISM: artificial sequence
<220> FEATURE:
<223> OTHER INFORMATION: synthesized oligonucleotide

<400> SEQUENCE: 10
cuucuuacua uguuucuagc ag                                              22

<210> SEQ ID NO 11
<211> LENGTH: 22
<212> TYPE: RNA
<213> ORGANISM: artificial sequence
<220> FEATURE:
<223> OTHER INFORMATION: synthesized oligonucleotide

<400> SEQUENCE: 11
aauuauugcc ucagcaauug ac                                              22

<210> SEQ ID NO 12
<211> LENGTH: 22
<212> TYPE: RNA
<213> ORGANISM: artificial sequence
<220> FEATURE:
<223> OTHER INFORMATION: synthesized oligonucleotide

<400> SEQUENCE: 12
aacuguaagu cguuugguug cc                                              22

<210> SEQ ID NO 13
<211> LENGTH: 24
<212> TYPE: RNA
<213> ORGANISM: artificial sequence
<220> FEATURE:
<223> OTHER INFORMATION: synthesized oligonucleotide

<400> SEQUENCE: 13
uguauaugag gcccaugcaa cugg                                            24

<210> SEQ ID NO 14
<211> LENGTH: 24
<212> TYPE: RNA
<213> ORGANISM: artificial sequence
<220> FEATURE:
<223> OTHER INFORMATION: synthesized oligonucleotide

<400> SEQUENCE: 14
gauccagcca uuugcuccau agcc                                            24
```

```
<210> SEQ ID NO 15
<211> LENGTH: 24
<212> TYPE: RNA
<213> ORGANISM: artificial sequence
<220> FEATURE:
<223> OTHER INFORMATION: synthesized oligonucleotide

<400> SEQUENCE: 15
caacaagcgg gucacuugaa ucgu                                              24

<210> SEQ ID NO 16
<211> LENGTH: 24
<212> TYPE: RNA
<213> ORGANISM: artificial sequence
<220> FEATURE:
<223> OTHER INFORMATION: synthesized oligonucleotide

<400> SEQUENCE: 16
gauauucgcg gcaacaacaa gcgg                                              24

<210> SEQ ID NO 17
<211> LENGTH: 20
<212> TYPE: RNA
<213> ORGANISM: artificial sequence
<220> FEATURE:
<223> OTHER INFORMATION: synthesized oligonucleotide

<400> SEQUENCE: 17
agaauguugc acauucucuc                                                   20

<210> SEQ ID NO 18
<211> LENGTH: 20
<212> TYPE: RNA
<213> ORGANISM: artificial sequence
<220> FEATURE:
<223> OTHER INFORMATION: synthesized oligonucleotide

<400> SEQUENCE: 18
cuuucucuca cuugauccac                                                   20

<210> SEQ ID NO 19
<211> LENGTH: 21
<212> TYPE: RNA
<213> ORGANISM: artificial sequence
<220> FEATURE:
<223> OTHER INFORMATION: synthesized oligonucleotide

<400> SEQUENCE: 19
caucgacucu ccuguauaug g                                                 21

<210> SEQ ID NO 20
<211> LENGTH: 20
<212> TYPE: RNA
<213> ORGANISM: artificial sequence
<220> FEATURE:
<223> OTHER INFORMATION: synthesized oligonucleotide

<400> SEQUENCE: 20
cauucuuaug auuucugccc                                                   20

<210> SEQ ID NO 21
<211> LENGTH: 20
<212> TYPE: RNA
<213> ORGANISM: artificial sequence
<220> FEATURE:
<223> OTHER INFORMATION: synthesized oligonucleotide
```

<400> SEQUENCE: 21
gguuuuuguc aguaucucgc                                               20

<210> SEQ ID NO 22
<211> LENGTH: 20
<212> TYPE: RNA
<213> ORGANISM: artificial sequence
<220> FEATURE:
<223> OTHER INFORMATION: synthesized oligonucleotide

<400> SEQUENCE: 22
ccuauuccac cauguuacag                                               20

<210> SEQ ID NO 23
<211> LENGTH: 20
<212> TYPE: RNA
<213> ORGANISM: artificial sequence
<220> FEATURE:
<223> OTHER INFORMATION: synthesized oligonucleotide

<400> SEQUENCE: 23
uuguuaauug ugauucugau                                               20

<210> SEQ ID NO 24
<211> LENGTH: 22
<212> TYPE: RNA
<213> ORGANISM: artificial sequence
<220> FEATURE:
<223> OTHER INFORMATION: synthesized oligonucleotide

<400> SEQUENCE: 24
aguugaacca aucuucuggu ug                                            22

<210> SEQ ID NO 25
<211> LENGTH: 23
<212> TYPE: DNA
<213> ORGANISM: artificial sequence
<220> FEATURE:
<223> OTHER INFORMATION: synthesized oligodeoxynucleotide

<400> SEQUENCE: 25
ggtattcttt ccagcaaata cat                                           23

<210> SEQ ID NO 26
<211> LENGTH: 23
<212> TYPE: DNA
<213> ORGANISM: artificial sequence
<220> FEATURE:
<223> OTHER INFORMATION: synthesized oligodeoxynucleotide

<400> SEQUENCE: 26
aatgttatct ccctcttaag ctt                                           23

<210> SEQ ID NO 27
<211> LENGTH: 23
<212> TYPE: DNA
<213> ORGANISM: artificial sequence
<220> FEATURE:
<223> OTHER INFORMATION: synthesized oligodeoxynucleotide

<400> SEQUENCE: 27
catgtcttat taatggatta gtt                                           23

<210> SEQ ID NO 28

-continued

```
<211> LENGTH: 23
<212> TYPE: DNA
<213> ORGANISM: artificial sequence
<220> FEATURE:
<223> OTHER INFORMATION: synthesized oligodeoxynucleotide

<400> SEQUENCE: 28
cgatcaataa tccacaatat cag                                              23

<210> SEQ ID NO 29
<211> LENGTH: 23
<212> TYPE: DNA
<213> ORGANISM: artificial sequence
<220> FEATURE:
<223> OTHER INFORMATION: synthesized oligodeoxynucleotide

<400> SEQUENCE: 29
tcttctttgt cataaaggat gag                                              23

<210> SEQ ID NO 30
<211> LENGTH: 23
<212> TYPE: DNA
<213> ORGANISM: artificial sequence
<220> FEATURE:
<223> OTHER INFORMATION: synthesized oligodeoxynucleotide

<400> SEQUENCE: 30
tgattaactc cattgctatt gtt                                              23

<210> SEQ ID NO 31
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 31
cttacttgat ccatcattgc cc                                               22

<210> SEQ ID NO 32
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 32
cattctcatt tgaagcaatc tg                                               22

<210> SEQ ID NO 33
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 33
gtcttctttc ttctcttttg tt                                               22

<210> SEQ ID NO 34
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 34
```
cttcttacta tgtttctagc ag                                              22

<210> SEQ ID NO 35
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 35
aattattgcc tcagcaattg ac                                              22

<210> SEQ ID NO 36
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 36
aactgtaagt cgtttggttg cc                                              22

<210> SEQ ID NO 37
<211> LENGTH: 24
<212> TYPE: DNA
<213> ORGANISM: artificial sequence
<220> FEATURE:
<223> OTHER INFORMATION: synthesized oligodeoxynucleotide

<400> SEQUENCE: 37
tgtatatgag gcccatgcaa ctgg                                            24

<210> SEQ ID NO 38
<211> LENGTH: 24
<212> TYPE: DNA
<213> ORGANISM: artificial sequence
<220> FEATURE:
<223> OTHER INFORMATION: synthesized oligodeoxynucleotide

<400> SEQUENCE: 38
gatccagcca tttgctccat agcc                                            24

<210> SEQ ID NO 39
<211> LENGTH: 24
<212> TYPE: DNA
<213> ORGANISM: artificial sequence
<220> FEATURE:
<223> OTHER INFORMATION: synthesized oligodeoxynucleotide

<400> SEQUENCE: 39
caacaagcgg gtcacttgaa tcgt                                            24

<210> SEQ ID NO 40
<211> LENGTH: 24
<212> TYPE: DNA
<213> ORGANISM: artificial sequence
<220> FEATURE:
<223> OTHER INFORMATION: synthesized oligodeoxynucleotide

<400> SEQUENCE: 40
gatattcgcg gcaacaacaa gcgg                                            24

<210> SEQ ID NO 41
<211> LENGTH: 20
<212> TYPE: DNA

```
<213> ORGANISM: artificial sequence
<220> FEATURE:
<223> OTHER INFORMATION: synthesized oligodeoxynucleotide

<400> SEQUENCE: 41
agaatgttgc acattctctc                                              20

<210> SEQ ID NO 42
<211> LENGTH: 20
<212> TYPE: DNA
<213> ORGANISM: artificial sequence
<220> FEATURE:
<223> OTHER INFORMATION: synthesized oligodeoxynucleotide

<400> SEQUENCE: 42
ctttctctca cttgatccac                                              20

<210> SEQ ID NO 43
<211> LENGTH: 21
<212> TYPE: DNA
<213> ORGANISM: artificial sequence
<220> FEATURE:
<223> OTHER INFORMATION: synthesized oligodeoxynucleotide

<400> SEQUENCE: 43
catcgactct cctgtatatg g                                            21

<210> SEQ ID NO 44
<211> LENGTH: 20
<212> TYPE: DNA
<213> ORGANISM: artificial sequence
<220> FEATURE:
<223> OTHER INFORMATION: synthesized oligodeoxynucleotide

<400> SEQUENCE: 44
cattcttatg atttctgccc                                              20

<210> SEQ ID NO 45
<211> LENGTH: 20
<212> TYPE: DNA
<213> ORGANISM: artificial sequence
<220> FEATURE:
<223> OTHER INFORMATION: synthesized oligodeoxynucleotide

<400> SEQUENCE: 45
ggtttttgtc agtatctcgc                                              20

<210> SEQ ID NO 46
<211> LENGTH: 20
<212> TYPE: DNA
<213> ORGANISM: artificial sequence
<220> FEATURE:
<223> OTHER INFORMATION: synthesized oligodeoxynucleotide

<400> SEQUENCE: 46
cctattccac catgttacag                                              20

<210> SEQ ID NO 47
<211> LENGTH: 20
<212> TYPE: DNA
<213> ORGANISM: artificial sequence
<220> FEATURE:
<223> OTHER INFORMATION: synthesized oligodeoxynucleotide

<400> SEQUENCE: 47
ttgttaattg tgattctgat                                              20
```

```
<210> SEQ ID NO 48
<211> LENGTH: 22
<212> TYPE: DNA
<213> ORGANISM: artificial sequence
<220> FEATURE:
<223> OTHER INFORMATION: synthesized oligodeoxynucleotide

<400> SEQUENCE: 48
agttgaacca atcttctggt tg                                              22
```

ANTI-INFLUENZA NUCLEIC ACID, PEPTIDE NUCLEIC ACID AND PREPARATIONS THEREOF

This is a National Phase Application filed under 35 U.S.C. 371 as a national stage of PCT/CN2012/082615, filed Oct. 9, 2012, the content of which is hereby incorporated by reference in its entirety.

TECHNICAL FIELD

The invention relates to an anti-influenza nucleic acid, a peptide nucleic acid and the preparations thereof.

The Sequence Listing submitted in text format (.txt) on Jul. 18, 2014, named "revision_1210017PCT_EnglishSequenceListing.txt", (created on Thursday, Jul. 17, 2014, 10 KB), is incorporated herein by reference.

BACKGROUND ART

Influenza virus is also known as IFV for short. Influenza virus is one of the earliest studied viruses and is received much concern due to its severe damage, which exhibits rapid outbreak and spread, and thus leads to local or global epidemics and disastrous consequences in a short period of time. There were 5 influenza outbreaks in the last century. In 1918, the Spanish Flu Pandemic (H1N1) had taken the lives of 20 million people. Later happened in 1957 was the Asian Flu, an influenza virus A H2N2 subtype derived from gene reassortment of human influenza viruses with avian influenza viruses, wherein three gene fragments, namely HA, NA, and PB1, came from avian influenza viruses, and other gene fragments came from human influenza viruses at the moment. The Hong Kong Flu, which was first found in Hong Kong and later spread to Japan and the United States, etc., killed many lives in 1968. Hong Kong Flu was influenza virus H3N3 subtype, which was also derived from gene reassortment of human influenza viruses with avian influenza viruses. The Russian Flu in 1977, derived from H1N1 subtype reassortment based on influenza virus A H5N1 subtype, spread relatively slow and mainly infected the youth and poultries. In 1998-1999, Hong Kong suffered again from influenza virus A H5N1 subtype epidemic. Furthermore, many lives of children and the old are taken by smaller epidemics every year, which results in serious social problems. Besides of epidemics in human being, influenza virus may also cause infection in animals, such as bird flu or swine flu etc., leading to tremendous economic loss in breeding industry. Starting from Southeast Asia in the winter of 2004, the H5N1 high pathogenic avian influenza resulted in grievous loss in many Asian and European countries and regions, and led to more than 100 cases of infections with more than 80 deaths all over the world. In 2007, the Mexican swine influenza gave rise to global attention. The frequent influenza epidemics are mainly because of the frequent variation of influenza virus, which makes the prevention and the control of influenza a great challenge to human beings.

Influenza viruses belong to Orthomyxoviridae, and are segmented minus-strand RNA viruses. According to different antigenicity of nucleocapsid protein (NP) and matrix protein (M), influenza viruses are divided into A, B and C types. The influenza viruses have a spherical shape with a diameter of 80-120 nm, whereas newly isolated strains are mostly filament-shaped with 400 nm in length. Influenza viruses comprise, from outside to inside, three parts of the envelope, the matrix protein and the core. The envelope is a phospholipid bilayer membrane coated outside of the matrix protein. The membrane is derived from cell membrane of the host, mature influenza virus buds from the host cell and separates from the cell after being coated outside with host cell membrane, to infect the next target. Except for phospholipid molecule, the envelope contains two important glycoproteins, namely hemagglutinin and neuraminidase, which extrude outside of the virus with 10-40 nm in length and are known as spikes. Usually there are 500 hemagglutinin spikes and 100 neuraminidase spikes on the surface of one influenza virus. In influenza virus A, the antigenicity of hemagglutinin and neuraminidase varies, which is a standard for distinction of viral strain subtypes.

Among three influenza viruses infecting human beings, influenza virus A has a very strong variability, and influenza virus B takes the second place; whereas the antigenicity of influenza virus C is very stable. As the most frequently varying type, influenza virus A intends to have a great antigenicity variation in every dozen years, which will result in a new virus strain. This variation is called antigenic shift, i.e., qualitative change of the antigen. Small changes also take place in influenza virus A by the form of point mutation in antigen amino acid sequence, which is called antigenic drift, i.e., quantitative change of the antigen. Antigenic shift may be a simultaneous change of both hemagglutinin antigen and neuraminidase antigen, which is called family variation; or, it may be a variation of hemagglutinin antigen only and neuraminidase antigen does not change or changes only a little, which is called subtype variation.

The influenza virus genome consists of 8 negative single stranded RNA fragments encoding 10 virus proteins, among which 8 are components for virus particles (HA, NA, NP, M1, M2, PB1, PB2 and PA), and the other two are RNA fragments with the smallest molecular weight encoding two non-structural proteins, namely, NS1 and NS2. NS1 relates to cytoplasm inclusion body. However, it is at present not very clear about functions of NS1 and NS2.

There are two glycoprotein spikes with different shapes and the same length of 10-20 nm on the surface of influenza virus A particles, respectively, hemagglutinin (HA) and neuraminidase (NA), both possessing antigenicity. The ratio of HA to NA is 4:1 to 5:1. There is also a transmembrane protein (M2 channel protein) of smaller amount on the surface of virus particles, the ratio of M2 to HA being 1:10-100. Located under the bilayer lipid envelope of virus particle is the matrix protein M1, whose content is the largest in the virus particle and which constitutes the main structure of the virus envelope. A complex of nucleic export protein (NEP, non-structural protein2, NS2) and viral ribonucleoprotein (RNP) is located inside of M1 and links thereto. The studies of the invention mainly focus on three genes of M, NP and PB2.

According to antigenicity of HA and NA, influenza virus A may be classified into different subtypes, among which there are 16 HAs (H1-16) and 9 NAs (N1-9). Avian influenza virus includes all subtypes, whereas human influenza virus includes only H1-H3 and N1-N2, and swine influenza virus includes only H1, H3, and N1-N2 subtypes.

As for genome of influenza virus, the genome of influenza virus A contains 8 RNA fragments (see FIG. 1), and at the 5' and 3' terminal of every fragment there is one non-encoding region, which is relatively conserved among all fragments and encodes one or more virus proteins. The biggest three RNA fragments encode polymerase, the 4$^{th}$ RNA fragment encodes HA protein, the 5$^{th}$ encodes NP protein, the 6$^{th}$ encodes NA and NB proteins (NB protein helps to infect), and the 7$^{th}$ encodes M1 protein (whose stop codon overlaps with the start codon of M2, to form a "stop-start" UAAUG sequence). The 8$^{th}$ fragment encodes NS1 as well as the NEP/NS2 protein through splice.

Due to the high variability of influenza, it is especially important to choose a silent target gene.

The matrix protein (MA) is a non-glycosylated structural protein, including two types, namely M1 and M2, and its structure is stable during the evolution of the virus. M1 regulates the export of ribonucleoprotein, and inhibits virus gene transcription as well as has the key effect thereof in virus budding and so on. M2 is a transmembrane protein with a conserved structure. M2 regulates pH gradients of transmembrane transportion tunnel of Golgi apparatus and stabilizes the HA protein. M1 consists of 252 amino acid residues with a molecular weight of about 26 kDa, and has no glycosylation site at the polypeptide chain. Except for being a structural protein, M1 participates in the regulation of virus transcription and the material delivery between the nucleus and cytoplasm of infected cells. M2 gene comprises two parts of 14-39 and 728-995, whose initial transcription product is cleaved of the 40-727 introns and spliced into mature mRNA, then translated into M2 protein. M2 protein is an intact membrane protein with 97 amino acids that is expressed massively at the surface of infected cells, including extracellular N-terminus (23 amino acid residues), transmembrane region (25-43 amino acid residues) and intracellular C-terminus (54 amino acid residues). M2 protein is a relatively smaller viral component, whose bioactive form is an oligo-tetramer. M2 protein includes 3 cysteine residues, Cys217, Cys219 and Cys250. Most M2 form an M2-dimer via a disulfide bond between Cys217 and Cys219, then a homotetramer via non-covalent bond linkage wherein Cys250 is acylated. Site specific mutation proves that although it is not a necessity for tetramer assembly, the disulfide bond can stabilize the M2 tetramer structure. If Cys217 and Cys219 are lacked, mutated tetramer can only play a role of cross-linking, and the virus may not survive or have weakened toxicity. M2 protein plays an important role in virus replication, and is also a target for anti-virus drugs.

Nucleoprotein (NP), a main protein component of virus nucleocapsid, is a monomer phosphorylated polypetide with a molecular weight of about 60 kDa and is type-specific, thus becoming a factor for the specified host selection. Encoded by vRNA fragment 5, nucleoprotein molecule consists of 498 amino acid residues and is rich in arginines. The amino acid sequence is conserved among subtypes and among various strains of one subtype, and provides basis for the evolution and classification of influenza virus molecules. Nucleoprotein, a main component of virus nucleocapsid, is type-specific and a chief antigen recognized by cytotoxic lymphocyte. It also plays a part in viral gene transcription and replication.

Structure and function of PB2 subunit: the PB2 subunit is another component of polymerase trimer and has many functions. On virus infection, the PB2 subunit determines host specificity of the virus by passing between cell nucleus and cytoplasm, the crucial site thereof being amino acid residue at position 702 [5]. The PB2 subunit also relates to viral pathogenicity wherein amino acid residue at position 627 plays a vital role. The D701N mutation can break the salt bridge between NSL and Arg753 of PB2, and potentially change the aggregation of 3 polymerase subunits, thus influences inter-species transmission of influenza viruses. When viral genome transcribes, the PB2 subunit can bind to cap structure. However, there is a controversy about the cap bonding site. Honda et al. (1999) believe that it relates to amino acid residues at position 242 and 252, Li et al. (2001) consider that it relates to amino acids in the region of 533-564, and Fechter et al. (2003) think that amino acid residues at position 363 and 404 are crucial ones for binding with cap structure, and 2 aromatic amino acids are extremely conserved in influenza virus A and B, which is of profound significance on the study of the function of influenza virus PB2 subunits of different subtypes. PB2 N-terminus links to PB1 C-terminus, wherein the amino acid residue at position 249 of PB2 plays a vital role. PB2 subunit recognizes the 5' terminus of vRNA promoter, specifically binds thereto, and cleaves the host cell mRNA as an endonuclease to create transcription primers, and thus starts viral genome transcription process which depends on the primer. However, the conclusion is still in dispute and needs more studies. PB2 is found to exist in the mitochondria of both transfected cells and virus infected cells. The positioning signal of PB2 in cell nucleus lies between 449-495 amino acid residues of PB2, and the target positioning signal is at the N-terminus thereof in the mitochondria. 2 conserved leucine residues play a vital role during this positioning process.

Among the several proteins of influenza virus, HA, NA, NP, M1 and M2 proteins work as virus structural proteins and participate in the assembly of virus particle, and play an important role in the maintenance of virus morphology, the assembly of capsomers, as well as the process of adsorption, invasion and release etc. of virus. NS1, NS2, PB1, PB2 and PA are non-structural proteins that do not directly participate in the assembly of virus capsomers, instead they exhibit important regulation effect in the virus replication cycle. Therefore, with thorough consideration of elements all around, the present invention is focused on conserved and important functional genes, such as M, NP and PB2.

Antisense nucleic acid includes antisense RNA and antisense DNA, and is characterized in its convenient synthesis, sequences being easily designed, modified, and high selectivity and affinity and so on. As a new anti-virus and anti-tumor drug, antisense nucleic acid raises a revolution in pharmacology field, namely, carries out the reaction after the binding of new drug receptor mRNA via new receptor binding mode (Watson-Crick hybridization), comprising (1) RNase H mediated degradation of target RNA; (2) inhibition of DNA replication and transcription as well as post-transcriptional processing and translation, etc. The antisense oligonucleotides (ODNs) treatment may exhibit higher specificity than traditional drug therapeutic tools. In the 30 years since late 1970s, antisense nucleic acid drugs have walked out of labs into practical clinical application. Antisense therapeutics has been paid more attention to especially after the first antisense nucleic acid drug, Fomivirsen, is approved to be listed in the market by FDA.

On the basis of base-pairing principles, antisense nucleic acid may participate in the regulation of related gene expression via base pairing with target RNA. The possible mode of regulation may be as follows: I. antisense RNA binds to virus mRNA, to form complementary double strand and block the binding of ribosome to virus mRNA, and thus inhibits process of virus mRNA being translated into protein; II. A triple helix nucleic acid can be formed by antisense DNA and the target gene, which regulates gene transcription by acting on transcriptons, enhancers and promoter regions controlling gene transcription; III. The binding of antisense nucleic acid to virus mRNA stops the delivery of mRNA to cytoplasm; IV. The binding of antisense nucleic acid to virus mRNA makes mRNA more easily to be recognized and degraded by nuclease, and thus greatly shortens mRNA half-lives. The above four pathways may exhibit as the inhibition or regulation on the virus gene expression, and this regulation is highly specific.

The antisense nucleic acid recognizes target gene on the basis of base-pairing principle. Theoretically, taking animal cells for an example, whose chromosomes have about several billions of base pairs, if the 4 bases (A, G, C and T) are roughly of the same amount and randomly distributed all over the gene, then it is not likely for antisense nucleic acids with more than 17 bases to hybridize with non-target gene, according to statistics principle. Therefore, it could be said that the binding of antisense nucleic acid molecules with more than 17 bases to target genes is unique, which results in high specificity of antisense nucleic acids.

Studies show that one gene copy will generate 200-300 mRNAs, which will then be translated into 100 thousand protein molecules with bioactivity. Traditional drugs mainly react with several sites of a certain domain in a bioactive protein molecule. However, because of the extremely complex protein structures and the various space structures of active proteins in an organism, it is actually not easy to get an ideal effect by controlling the dynamic and integral function of target molecules via several limited kinds of acting sites of the traditional drugs and the limitation of the traditional drugs is obvious. The mRNA can be translated into tens to hundreds of proteins, and antisense nucleic acids regulate the target gene directly at mRNA level, which equals to amply the effect of the traditional drugs by tens to hundreds of times, from which it can be seen that the regulation of the antisense nucleic acids is extremely economic and reasonable.

Toxicology researches show that, antisense nucleic acids exhibit low toxicity in vivo. In spite of longer or shorter retention time in vivo, antisense nucleic acids are all eliminated by degradation, avoiding risks of foreign gene integration into host chromosomes, such as what happened in transgenetic therapy. Compared to traditional drugs, antisense nucleic acid drugs show advantages of high specificity and efficiency as well as low toxic and side effect and so on, and exhibit good application value at various aspects, such as tumor inhibition and virus replication resistance, etc. Nowadays there are multiple antisense nucleic acid drugs in American and European markets, and 30 more at preclinical develop phase or experimental phase I, II or III after develop.

Because of a plenty of exonucleases existed in animals, antisense nucleic acids without chemical modification are easily to be degraded and lose activities. At present, there are many approaches for chemical modification of antisense nucleic acids, such as sulfo-modification and 2'-methoxy modification, etc. Being most thoroughly studied at present, sulfo-modified drugs can effectively resist degradation of nuclease and promote the activity of nuclease Rase H, said modification method having been successfully used in clinical antisense nucleic acid drugs. However, these are only the first generation of antisense nucleic acid modification method, and new modification approaches and methods are developed with technology development, leading to second and third generations of antisense nucleic acid modification, in which peptide framework modification is most eye-catching.

Peptide nucleic acids (PNAs), a brand new DNA analog with neutral amido bond as framework, may target DNA big grooves in specific sequence. The structural unit of PNA framework is N (2-aminoethyl)-glycine, and base groups link to the amino N atom of main framework by a methylene carbonyl group. PNA is the second generation product of the antisense nucleic acid.

As a natural cationic polymer, chitosan (cs) is not only easy to bind with genetic materials such as genes (nucleic acids) to form nano-particles, but also has advantages such as non-toxicity, easily availability, biodegradability, stability, biocompatibility, gastrointestinal environment (pH, nuclease) destruction resistibility, strong bioadhesiveness, and being able to promote the permeating and adsorbing of the drugs, etc., therefore becoming a good carrier for oral-taken gene drugs.

SUMMARY OF THE INVENTION

The aim of the invention is to provide an antisense nucleic acid, an antisense peptide nucleic acid and the preparations thereof against anti-influenza virus, which is of high bioavailability, stable physical and chemical properties and high efficiency.

An anti-influenza virus H1N1 antisense nucleic acid, selected from one or more of the following sequences:

```
H1N1-M
SEQ ID NO: 1:
5'-GGUAUUCUUUCCAGCAAAUACAU-3';

SEQ ID NO: 2:
5'-AAUGUUAUCUCCCUCUUAAGCUU-3';

SEQ ID NO: 3:
5'-CAUGUCUUAUUAAUGGAUUAGUU-3';

SEQ ID NO: 4:
5'-CGAUCAAUAAUCCACAAUAUCAG-3';

H1N1-NP
SEQ ID NO: 5:
5'-UCUUCUUUGUCAUAAAGGAUGAG-3';

SEQ ID NO: 6:
5'-UGAUUAACUCCAUUGCUAUUGUU-3';

SEQ ID NO: 7:
5'-UCUUACUUGAUCCAUCAUUGCCC-3;

SEQ ID NO: 8:
5'-ACAUUCUCAUUUGAAGCAAUCUG-3;

H1N1-PB2
SEQ ID NO: 9:
5'-CGUCUUCUUUCUUCUCUUUUGUU-3;

SEQ ID NO: 10:
5'-UCUUCUUACUAUGUUUCUAGCAG-3;

SEQ ID NO: 11:
5'-CAAUUAUUGCCUCAGCAAUUGAC-3;

SEQ ID NO: 12:
5'-GAACUGUAAGUCGUUUGGUUGCC-3;
```

An anti-influenza virus H3N2 antisense nucleic acid, selected from one or more of the following sequences:

```
H3N2-M
SEQ ID NO: 13:
5'-UUGUAUAUGAGGCCCAUGCAACUGG-3';

SEQ ID NO: 14:
5'-UGAUCCAGCCAUUUGCUCCAUAGCC-3';

SEQ ID NO: 15:
5'-ACAACAAGCGGGUCACUUGAAUCGU-3';

SEQ ID NO: 16:
5'-UGAUAUUCGCGGCAACAACAAGCGG-3';

H3N2-NP
SEQ ID NO: 17:
5'-AAGAAUGUUGCACAUUCUCUC-3';
```

```
SEQ ID NO: 18:
5'-ACUUUCUCUCACUUGAUCCAC-3';

SEQ ID NO: 19:
5'-CCAUCGACUCUCCUGUAUAUGG-3';

SEQ ID NO: 20:
5'-UCAUUCUUAUGAUUUCUGCCC-3';

H3N2-PB2
SEQ ID NO: 21:
5'-UGGUUUUUGUCAGUAUCUCGC-3';

SEQ ID NO: 22:
5'-UCCUAUUCCACCAUGUUACAG-3';

SEQ ID NO: 23:
5'-AUUGUUAAUUGUGAUUCUGAU-3';

SEQ ID NO: 24:
5'-GAGUUGAACCAAUCUUCUGGUUG-3'.
```

Preferable sequences selected through experiments from the above-designed antisense nucleic acids of the invention are as follows (SEQ ID NO: 1, 5, 6 and 12 for H1N1), (SEQ ID NO: 15, 16, 17, 20, 22 and 23 for H3N2):

```
H1N1
SEQ ID NO: 1:
5'-GGUAUUCUUUCCAGCAAAUACAU-3';

SEQ ID NO: 5:
5'-UCUUCUUUGUCAUAAAGGAUGAG-3';

SEQ ID NO: 6:
5'-UGAUUAACUCCAUUGCUAUUGUU-3';

SEQ ID NO: 12:
5'-GAACUGUAAGUCGUUUGGUUGCC-3';

H3N2
SEQ ID NO: 15:
5'-ACAACAAGCGGGUCACUUGAAUCGU-3';

SEQ ID NO: 16:
5'-UGAUAUUCGCGGCAACAACAAGCGG-3';

SEQ ID NO: 17:
5'-AAGAAUGUUGCACAUUCUCUC-3';

SEQ ID NO: 20:
5'-UCAUUCUUAUGAUUUCUGCCC-3';

SEQ ID NO: 22:
5'-UCCUAUUCCACCAUGUUACAG-3';

SEQ ID NO: 23:
5'-AUUGUUAAUUGUGAUUCUGAU-3'.
```

An anti-influenza virus H1N1 antisense peptide nucleic acid, selected from one or more of the following sequences:

```
H1N1-M
SEQ ID NO: 25:
5'-GGTATTCTTTCCAGCAAATACAT-3';

SEQ ID NO: 26:
5'-AATGTTATCTCCCTCTTAAGCTT-3';

SEQ ID NO: 27:
5'-CATGTCTTATTAATGGATTAGTT-3';

SEQ ID NO: 28:
5'-CGATCAATAATCCACAATATCAG-3';

H1N1-NP
SEQ ID NO: 29:
5'-TCTTCTTTGTCATAAAGGATGAG-3';

SEQ ID NO: 30:
5'-TGATTAACTCCATTGCTATTGTT-3';

SEQ ID NO: 31:
5'-TCTTACTTGATCCATCATTGCCC-3;

SEQ ID NO: 32:
5'-ACATTCTCATTTGAAGCAATCTG-3';

H1N1-PB2
SEQ ID NO: 33:
5'-CGTCTTCTTTCTTCTCTTTTGTT-3';

SEQ ID NO: 34:
5'-TCTTCTTACTATGTTTCTAGCAG-3';

SEQ ID NO: 35:
5'-CAATTATTGCCTCAGCAATTGAC-3';

SEQ ID NO: 36:
5'-GAACTGTAAGTCGTTTGGTTGCC-3;
```

An anti-influenza virus H3N2 antisense peptide nucleic acid, selected from one or more of the following sequences:

```
H3N2-M
SEQ ID NO: 37:
5'-TTGTATATGAGGCCCATGCAACTGG-3';

SEQ ID NO: 38:
5'-TGATCCAGCCATTTGCTCCATAGCC-3';

SEQ ID NO: 39:
5'-ACAACAAGCGGGTCACTTGAATCGT-3';

SEQ ID NO: 40:
5'-TGATATTCGCGGCAACAACAAGCGG-3';

H3N2-NP
SEQ ID NO: 41:
5'-AAGAATGTTGCACATTCTCTC-3';

SEQ ID NO: 42:
5'-ACTTTCTCTCACTTGATCCAC-3';

SEQ ID NO: 43:
5'-CCATCGACTCTCCTGTATATGG-3';

SEQ ID NO: 44:
5'-TCATTCTTATGATTTCTGCCC-3';

H3N2-PB2
SEQ ID NO: 45:
5'-TGGTTTTTGTCAGTATCTCGC-3';

SEQ ID NO: 46:
5'-TCCTATTCCACCATGTTACAG-3';

SEQ ID NO: 47:
5'-ATTGTTAATTGTGATTCTGAT-3';

SEQ ID NO: 48:
5'-GAGTTGAACCAATCTTCTGGTTG-3'.
```

Preferable sequences selected through experiments from the above-designed antisense peptide nucleic acids of the invention are as follows (SEQ ID NO: 25, 29, 30 and 36 for H1N1), (SEQ ID NO: 39, 40, 41, 44, 46 and 47 for H3N2).

```
H1N1
SEQ ID NO: 25:
5'-GGTATTCTTTCCAGCAAATACAT-3';
```

-continued

SEQ ID NO: 29:
5'-TCTTCTTTGTCATAAAGGATGAG-3';

SEQ ID NO: 30:
5'-TGATTAACTCCATTGCTATTGTT-3';

SEQ ID NO: 36:
5'-GAACTGTAAGTCGTTTGGTTGCC-3;

H3N2
SEQ ID NO: 39:
5'-ACAACAAGCGGGTCACTTGAATCGT-3';

SEQ ID NO: 40:
5'-TGATATTCGCGGCAACAACAAGCGG-3';

SEQ ID NO: 41:
5'-AAGAATGTTGCACATTCTCTC-3';

SEQ ID NO: 44:
5'-TCATTCTTATGATTTCTGCCC-3';

SEQ ID NO: 46:
5'-TCCTATTCCACCATGTTACAG-3';

SEQ ID NO: 47:
5'-ATTGTTAATTGTGATTCTGAT-3'.

The peptide nucleic acid of the invention exists in the form of DNA and has high binding efficiency which is the characteristic of peptide nucleic acid.

The antisense nucleic acid or the antisense peptide nucleic acid of the invention may be further prepared into antisense nucleic acid or antisense peptide nucleic acid preparations with the addition of pharmaceutically acceptable carriers or excipients. For example, the nucleic acid or the peptide nucleic acid may be spray-dried into micro-capsule with chitosan, with brief steps as follows: nucleic acid or peptide nucleic acid and chitosan are respectively dissolved in glacial acetic acid-water-acetone to obtain a chitosan solution, and then 1% of glutaraldehyde solution is added as a cross-linking agent; the resulting liquid is then subjected to spray-drying in inert hot air, wherein the liquid is atomized by compressed air after being delivered to spray nozzle by peristaltic pump, then blew into a cavity together with hot air, with the glacial acetic acid-water-acetone being rapidly evaporated, so that drug-containing chitosan microsphere is formed. It is utilized in this invention for the study of preparation of anti-influenza virus drugs.

The anti-influenza virus antisense nucleic acid and antisense peptide nucleic acid of the invention are of high bioavailability and stable physical and chemical properties with no toxic or side effect and no drug tolerance, capable of inhibiting influenza virus replication with good anti-virus effect and low cost.

In the invention, virus specified antisense oligonucleotide sequence is designed according to conserved regions of genes of the three proteins of influenza virus, namely M2 matrix protein, nucleoprotein and polymerase. The antisense oligonucleotide is artificially synthesized, peptide modified and chitosan packaged, to obtain high bioavailability, stable physical and chemical properties and good anti-virus effect.

Figure 1:
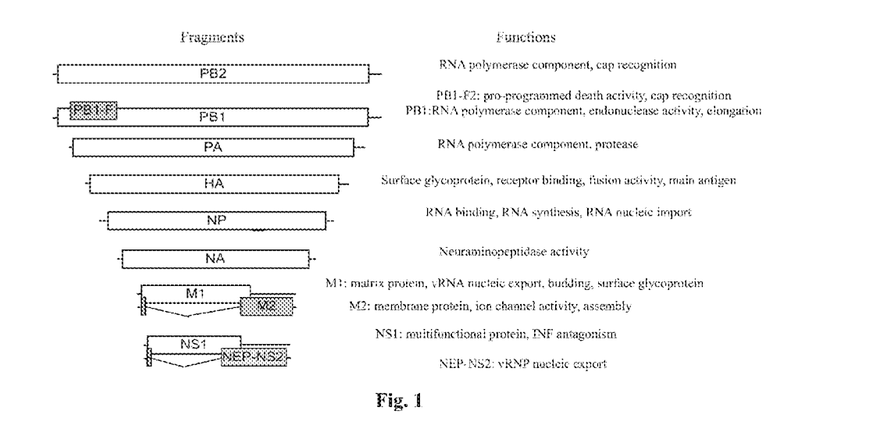
FIG. 1: Schematic diagram of 8 RNA fragments contained in influenza virus A genome.
Figure 2:
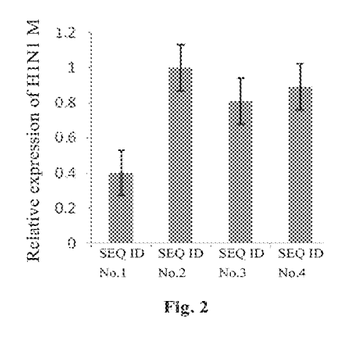
FIG. 2: Inhibition efficiency of PNA against the H1N1 M gene.
Figure 3:
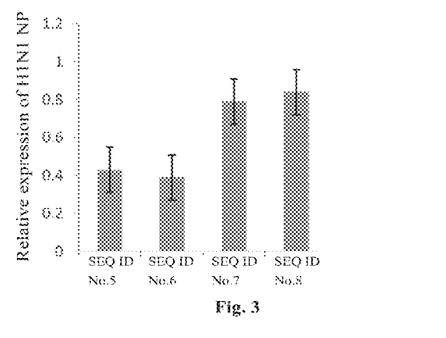
FIG. 3: Inhibition efficiency of PNA against the H1N1 NP gene.
Figure 4:
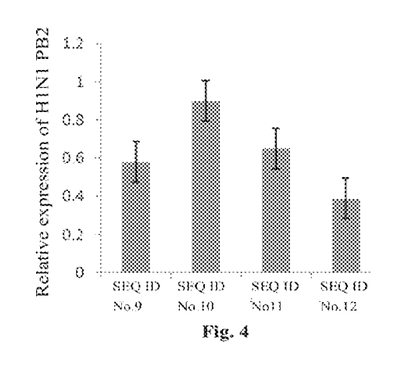
FIG. 4: Inhibition efficiency of PNA against the H1N1 PB2 gene.
Figure 5:
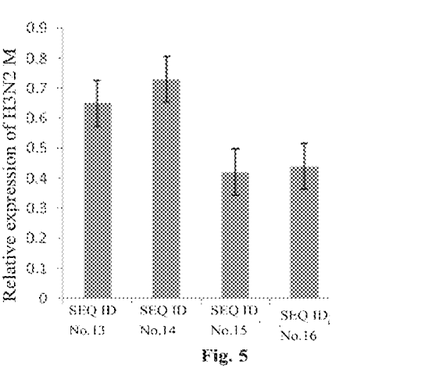
FIG. 5: Inhibition efficiency of PNA against the H3N2 M gene.
Figure 6:
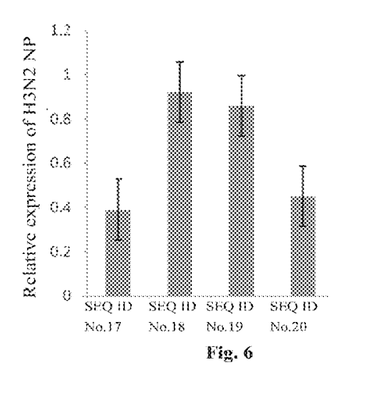
FIG. 6: Inhibition efficiency of PNA against the H3N2 NP gene.
Figure 7:
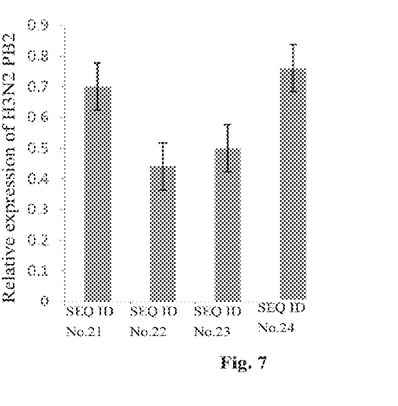
FIG. 7: Inhibition efficiency of PNA against the H3N2 PB2 gene.

Wherein, the corresponding gene functions in FIG. 1 are as follows:

PB2 RNA polymerase component, cap recognition
PB1 PB1-F2: pro-programmed death activity, cap recognition
PB1: RNA polymerase component, endonuclease activity, elongation
PA RNA polymerase component, protease
HA surface glycoprotein, receptor binding, fusion activity, main antigen
NP RNA binding, RNA synthesis, RNA nucleic import
NA neuraminopeptidase activity
M1: matrix protein, vRNA nucleic export, budding, surface glycoprotein
M2: membrane protein, ion channel activity, assembly
NS1: multifunctional protein, INF antagonism
NEP-NS2: vRNP nucleic export

DETAILED DESCRIPTION OF THE PREFERRED EMBODIMENT

Antisense nucleic acids with following sequences (purchased from Invitrogen Corp.) were:

H1N1-M
SEQ ID NO: 1:
5'-GGUAUUCUUUCCAGCAAAUACAU-3';

SEQ ID NO: 2:
5'-AAUGUUAUCUCCCUCUUAAGCUU-3';

SEQ ID NO: 3:
5'-CAUGUCUUAUUAAUGGAUUAGUU-3';

SEQ ID NO: 4:
5'-CGAUCAAUAAUCCACAAUAUCAG-3';

H1N1-NP
SEQ ID NO: 5:
5'-UCUUCUUUGUCAUAAAGGAUGAG-3';

SEQ ID NO: 6:
5'-UGAUUAACUCCAUUGCUAUUGUU-3';

SEQ ID NO: 7:
5'-UCUUACUUGAUCCAUCAUUGCCC-3;

SEQ ID NO: 8:
5'-ACAUUCUCAUUUGAAGCAAUCUG-3;

H1N1-PB2
SEQ ID NO: 9:
5'-CGUCUUCUUUCUUCUCUUUUGUU-3;

SEQ ID NO: 10:
5'-UCUUCUUACUAUGUUUCUAGCAG-3;

SEQ ID NO: 11:
5'-CAAUUAUUGCCUCAGCAAUUGAC-3;

SEQ ID NO: 12:
5'-GAACUGUAAGUCGUUUGGUUGCC-3;

-continued

H3N2-M
SEQ ID NO: 13:
5'-UUGUAUAUGAGGCCCAUGCAACUGG-3';

SEQ ID NO: 14:
5'-UGAUCCAGCCAUUUGCUCCAUAGCC-3';

SEQ ID NO: 15:
5'-ACAACAAGCGGGUCACUUGAAUCGU-3';

SEQ ID NO: 16:
5'-UGAUAUUCGCGGCAACAACAAGCGG-3';

H3N2-NP
SEQ ID NO: 17:
5'-AAGAAUGUUGCACAUUCUCUC-3';

SEQ ID NO: 18:
5'-ACUUUCUCUCACUUGAUCCAC-3';

SEQ ID NO: 19:
5'-CCAUCGACUCUCCUGUAUAUGG-3';

SEQ ID NO: 20:
5'-UCAUUCUUAUGAUUUCUGCCC-3';

H3N2-PB2
SEQ ID NO: 21:
5'-UGGUUUUUGUCAGUAUCUCGC-3';

SEQ ID NO: 22:
5'-UCCUAUUCCACCAUGUUACAG-3';

SEQ ID NO: 23:
5'-AUUGUUAAUUGUGAUUCUGAU-3';

SEQ ID NO: 24:
5'-GAGUUGAACCAAUCUUCUGGUUG-3'.

Peptide nucleic acids of antisense nucleic acids with following sequences were purchased from CP BIOCHEM Corp.:

H1N1-M
SEQ ID NO: 25:
5'-GGTATTCTTTCCAGCAAATACAT-3';

SEQ ID NO: 26:
5'-AATGTTATCTCCCTCTTAAGCTT-3';

SEQ ID NO: 27:
5'-CATGTCTTATTAATGGATTAGTT-3';

SEQ ID NO: 28:
5'-CGATCAATAATCCACAATATCAG-3';

H1N1-NP
SEQ ID NO: 29:
5'-TCTTCTTTGTCATAAAGGATGAG-3';

SEQ ID NO: 30:
5'-TGATTAACTCCATTGCTATTGTT-3';

SEQ ID NO: 31:
5'-TCTTACTTGATCCATCATTGCCC-3';

SEQ ID NO: 32:
5'-ACATTCTCATTTGAAGCAATCTG-3';

H1N1-PB2
SEQ ID NO: 33:
5'-CGTCTTCTTTCTTCTCTTTTGTT-3';

SEQ ID NO: 34:
5'-TCTTCTTACTATGTTTCTAGCAG-3';

SEQ ID NO: 35:
5'-CAATTATTGCCTCAGCAATTGAC-3';

-continued

SEQ ID NO: 36:
5'-GAACTGTAAGTCGTTTGGTTGCC-3;

H3N2-M
SEQ ID NO: 37:
5'-TTGTATATGAGGCCCATGCAACTGG-3';

SEQ ID NO: 38:
5'-TGATCCAGCCATTTGCTCCATAGCC-3';

SEQ ID NO: 39:
5'-ACAACAAGCGGGTCACTTGAATCGT-3';

SEQ ID NO: 40:
5'-TGATATTCGCGGCAACAACAAGCGG-3';

H3N2-NP
SEQ ID NO: 41:
5'-AAGAATGTTGCACATTCTCTC-3';

SEQ ID NO: 42:
5'-ACTTTCTCTCACTTGATCCAC-3';

SEQ ID NO: 43:
5'-CCATCGACTCTCCTGTATATGG-3';

SEQ ID NO: 44:
5'-TCATTCTTATGATTTCTGCCC-3';

H3N2-PB2
SEQ ID NO: 45:
5'-TGGTTTTTGTCAGTATCTCGC-3';

SEQ ID NO: 46:
5'-TCCTATTCCACCATGTTACAG-3';

SEQ ID NO: 47:
5'-ATTGTTAATTGTGATTCTGAT-3';

SEQ ID NO: 48:
5'-GAGTTGAACCAATCTTCTGGTTG-3'.

The above antisense nucleic acids and the peptide nucleic acids thereof (purchased from CP BIOCHEM Corp.) were spray-dried to form micro-capsules with chitosan, through brief steps as follows: antisense nucleic acids or peptide nucleic acids and chitosan were respectively dissolved in glacial acetic acid-water-acetone to obtain chitosan solutions, and then 1% of glutaraldehyde solution was added as a cross-linking agent. The resulting liquid was then subjected to spray-drying in inert hot air, wherein the liquid was atomized by compressed air as being delivered to spray nozzle by peristaltic pump, then blew into a cavity together with hot air, the glacial acetic acid-water-acetone in the mixture being rapidly evaporated, so that drugs-containing chitosan microsphere is formed.

Influenza strain: H1N1 and H3N2
Cell line: Madin-Darby canine kidney (MDCK)
Nucleic acid: 1. µg/ml
Peptide nucleic acid: 1.5 µg/ml.
Detection primers

| Target gene | Primer pairs/ probe set | Sequence (5'-3') |
| --- | --- | --- |
| H1-HA | H1-F | AACTACTACTGGACTCTGCTGGAA |
| | H1-R | CCATTGGTGCATTTGAGGTGATG |
| | H1M-F | CGATTCCCAGCATAAGTCT |
| | H1M-R | GCCTGATTAGCAACCTCCA |
| | H1NP-F | AGGAAACGCTGAGATTGAA |
| | H1NP-R | CTATCCCGACCAGTGAGTA |
| | H1PB2-F | TTTTGGTGGGTTCACTTTC |
| | H1PB2-R | AATCTCCTGGTTGCCTTTC |

-continued

| | | |
|---|---|---|
| H3-HA | H3-F | AAGCATTCCYAATGACAAACC |
| | H3-R | ATTGCRCCRAATATGCCTCTAGT |
| | H3M-F | AAGATGAGCCTTCTAACCG |
| | H3M-R | CTTGTCTTTAGCCATTCCA |
| | H3NP-F | TTGCTCACAAATCTTGCCTAC |
| | H3NP-R | TCCTCCACTCCTGGTCCTT |
| | H3PB2-F | GAGTGGAGTCCGCCGTCTT |
| | H3PB2-R | CTCCTTGCCCGATTAGCAC |
| β-actin | Actin-F | GCGGGAAATCGTGCGTGAC |
| | Actin-R | TGGGAGGAAACAGAAGTGGAA |

Viral target gene inhibition degree of peptide nucleic acids was detected by influenza virus specified quantitative RT-PCR, and classical hemagglutination assay was performed to detect anti-virus titer.

Day 1:

Inoculation: early prepared MDCK cells were digested, collected by centrifugation, counted, regulated to $1\times10^5$/ml with complete medium and inoculated onto 24-well plates, then cultured in a 37° C., carbon dioxide chamber for 18-24 hours.

Day 2:

Cell density was observed by microscope till cells grew up to 70~80% of plate area in good condition. Culture solution was removed and 300 μl of drugs (including two forms of the nucleic acid and the peptide nucleic acid) was added into every well to be selected, 10 wells for each drug. After incubation for 1 hour, 100 μl of influenza virus (with infection ratio of 0.01) was added for 2 hours adsorption. Complete medium was added after unadsorbed virus was washed with nutrient solution, and then cultured again in a 37° C., 5% carbon dioxide environment. After 36 h and 72 h of infection, respectively, infected cells were subjected to multiple freeze-thaw to release virus, which was used as samples for virus assay. During experiments, there were also a normal cell control group without virus and the nucleic acid or the peptide nucleic acid, a virus group with virus and without the nucleic acid or the peptide nucleic acid, and a negative control group with the nucleic acid or the peptide nucleic acid and without virus.

Days 3-5:

Protection effect of drugs on cells was observed and results were evaluated.

Quantitative Real-Time PCR Assay

Supernatants from above groups were collected and virus RNA was extracted with total RNA isolation kit. Resulting virus RNA was first reversely transcribed into cDNA, and then virus contents in H1N1 and H3N2 groups was detected respectively using primers against H1 and H3. After quantitative amplification, virus titers and inhibition effect in each group, as well as the ratio of treatment group vs. virus infection group were calculated with statistics software. The inhibition degrees of antisense peptide nucleic acid groups of SEQ ID NO: 25-48 on viral target gene were shown in FIGS. 2-7, wherein Y-axis stood for the relative expression level of viral target gene.

| Reaction system (25 μl) | |
|---|---|
| Reagents | Dosages (ul) |
| 2 × One-Step RT-PCR Buffer | 12.5 |
| Ex TaqTM HS | 0.5 |
| PrimeScriptTM RT Enzyme Mix II | 0.5 |

| Reaction system (25 μl) | |
|---|---|
| Reagents | Dosages (ul) |
| PCR Forward Primer | 0.5 |
| PCR Reverse Primer | 0.5 |
| Total RNA | 2 |
| RNase Free dH2O | 8.5 |
| Total | 25 |

Reaction Conditions:

Reverse transcription

42° C. 5 min

95° C. 10 sec

PCR amplification

Cycle: 40

95° C. 5 sec

60° C. 30 sec

Hemagglutination Titer Assay

Hemagglutination assay was performed as routine methods. The samples of lysis solution were harvested after 36 h and 72 h of transfection, hemagglutination titers were detected for control group and each of the antisense nucleic acid and the antisense peptide nucleic acid group by HA test, and inhibition efficiency were calculated using the formula [(HA control-HA test)/HA control]×100.

Screening results of experimental groups were shown in tables 1-4.

TABLE 1

Analysis on anti-H1N1 virus activity of anti-influenza virus antisense nucleic acid in cells

| | Treatment Antisense | Hemagglutination titers | | Virus inhibition |
|---|---|---|---|---|
| NOs | nucleic acids | 36 h | 72 h | (%) |
| 1 | SEQ ID NO: 1 | 14 ± 2 | 33 ± 2 | 65%-81% |
| 2 | SEQ ID NO: 2 | 49 ± 5 | 256 ± 5 | 25%-31% |
| 3 | SEQ ID NO: 3 | 28 ± 2 | 98 ± 2 | 50%-59% |
| 4 | SEQ ID NO: 4 | 34 ± 2 | 120 ± 3 | 40%-50% |
| 5 | SEQ ID NO: 5 | 22 ± 1 | 64 ± 4 | 62%-75% |
| 6 | SEQ ID NO: 6 | 16 ± 2 | 32 ± 2 | 68%-85% |
| 7 | SEQ ID NO: 7 | 23 ± 3 | 100 ± 3 | 51%-69% |
| 8 | SEQ ID NO: 8 | 41 ± 4 | 136 ± 4 | 38%-46% |
| 9 | SEQ ID NO: 9 | 27 ± 3 | 92 ± 3 | 61%-86% |
| 10 | SEQ ID NO: 10 | 49 ± 5 | 185 ± 5 | 23%-28% |
| 11 | SEQ ID NO: 11 | 36 ± 4 | 106 ± 4 | 47%-58% |
| 12 | SEQ ID NO: 12 | 15 ± 4 | 32 ± 4 | 75%-87% |
| 13 | Virus group | 64 | 256 | 0 |
| 14 | Negative control group | 0 | 0 | 0 |
| 15 | Normal cell control group | 0 | 0 | 0 |

TABLE 2

Analysis on anti-H1N1 virus activity of anti-influenza virus antisense peptide nucleic acid in cells

| | Treatment Antisense peptide | Hemagglutination titers | | Virus inhibition |
|---|---|---|---|---|
| NOs | nucleic acids | 36 h | 72 h | (%) |
| 1 | SEQ ID NO: 25 | 16 ± 2 | 32 ± 2 | 75%-87% |
| 2 | SEQ ID NO: 26 | 48 ± 5 | 176 ± 5 | 25%-31% |
| 3 | SEQ ID NO: 27 | 30 ± 4 | 104 ± 4 | 53%-59% |

TABLE 2-continued

Analysis on anti-H1N1 virus activity of anti-influenza
virus antisense peptide nucleic acid in cells

| NOs | Treatment Antisense peptide nucleic acids | Hemagglutination titers 36 h | Hemagglutination titers 72 h | Virus inhibition (%) |
|---|---|---|---|---|
| 4 | SEQ ID NO: 28 | 38 ± 4 | 128 ± 4 | 40%-50% |
| 5 | SEQ ID NO: 29 | 21 ± 2 | 64 ± 4 | 67%-75% |
| 6 | SEQ ID NO: 30 | 18 ± 2 | 30 ± 2 | 71%-88% |
| 7 | SEQ ID NO: 31 | 29 ± 3 | 98 ± 3 | 54%-62% |
| 8 | SEQ ID NO: 32 | 40 ± 4 | 138 ± 4 | 38%-46% |
| 9 | SEQ ID NO: 33 | 24 ± 3 | 88 ± 3 | 62%-66% |
| 10 | SEQ ID NO: 34 | 49 ± 5 | 185 ± 5 | 23%-28% |
| 11 | SEQ ID NO: 35 | 34 ± 4 | 108 ± 4 | 47%-58% |
| 12 | SEQ ID NO: 36 | 16 ± 2 | 32 ± 2 | 75%-87% |
| 13 | Virus group | 64 | 256 | 0 |
| 14 | Negative control group | 0 | 0 | 0 |
| 15 | Normal cell control group | 0 | 0 | 0 |

The above cell-virus experiment results showed that, antisense nucleic acids of SEQ ID NO: 1-12 and peptide nucleic acids of SEQ ID NO: 25-36 all had anti-H1N1 activities; wherein SEQ ID NO: 1, SEQ ID NO: 5, SEQ ID NO: 6, SEQ ID NO: 12 exhibited stronger anti-H1N1 activities.

Preferable sequences selected were mixed by equal mass ratio, and then the anti-H1N1 effect of the mixture was detected. Results showed that, the hemagglutination titer in 36 h was 16±2, and that in 72 h was 30±2. The virus inhibition was 71%-89%.

TABLE 3

Analysis on anti-H3N2 virus activity of anti-influenza
virus antisense nucleic acid in cells

| NOs | Treatment Antisense nucleic acids | Hemagglutination titers 36 h | Hemagglutination titers 72 h | Virus inhibition (%) |
|---|---|---|---|---|
| 1 | SEQ ID NO: 13 | 72 ± 5 | 215 ± 5 | 39%-47% |
| 2 | SEQ ID NO: 14 | 79 ± 5 | 227 ± 5 | 35%-38% |
| 3 | SEQ ID NO: 15 | 18 ± 2 | 87 ± 4 | 57%-78% |
| 4 | SEQ ID NO: 16 | 21 ± 3 | 78 ± 3 | 62%-76% |
| 5 | SEQ ID NO: 17 | 18 ± 2 | 56 ± 2 | 70%-85% |
| 6 | SEQ ID NO: 18 | 50 ± 4 | 188 ± 4 | 38%-47% |
| 7 | SEQ ID NO: 19 | 72 ± 5 | 245 ± 5 | 19%-26% |
| 8 | SEQ ID NO: 20 | 24 ± 2 | 85 ± 4 | 54%-76% |
| 9 | SEQ ID NO: 21 | 48 ± 4 | 158 ± 4 | 41%-50% |
| 10 | SEQ ID NO: 22 | 27 ± 2 | 42 ± 2 | 61%-78% |
| 11 | SEQ ID NO: 23 | 28 ± 2 | 77 ± 4 | 72%-89% |
| 12 | SEQ ID NO: 24 | 48 ± 4 | 178 ± 4 | 39%-50% |
| 13 | Virus group | 64 | 256 | 0 |
| 14 | Negative control group | 0 | 0 | 0 |
| 15 | Normal cell control group | 0 | 0 | 0 |

TABLE 4

Analysis on anti-H3N2 virus activity of anti-influenza
virus antisense peptide nucleic acid in cells

| NOs | Treatment Antisense peptide nucleic acids | Hemagglutination titers 36 h | Hemagglutination titers 72 h | Virus inhibition (%) |
|---|---|---|---|---|
| 1 | SEQ ID NO: 37 | 52 ± 5 | 195 ± 5 | 19%-23% |
| 2 | SEQ ID NO: 38 | 49 ± 5 | 185 ± 5 | 23%-28% |

TABLE 4-continued

Analysis on anti-H3N2 virus activity of anti-influenza
virus antisense peptide nucleic acid in cells

| NOs | Treatment Antisense peptide nucleic acids | Hemagglutination titers 36 h | Hemagglutination titers 72 h | Virus inhibition (%) |
|---|---|---|---|---|
| 3 | SEQ ID NO: 39 | 21 ± 2 | 64 ± 4 | 67%-75% |
| 4 | SEQ ID NO: 40 | 24 ± 3 | 88 ± 3 | 62%-66% |
| 5 | SEQ ID NO: 41 | 19 ± 2 | 36 ± 2 | 70%-86% |
| 6 | SEQ ID NO: 42 | 40 ± 4 | 138 ± 4 | 38%-46% |
| 7 | SEQ ID NO: 43 | 52 ± 5 | 195 ± 5 | 19%-23% |
| 8 | SEQ ID NO: 44 | 28 ± 2 | 75 ± 4 | 56%-71% |
| 9 | SEQ ID NO: 45 | 38 ± 4 | 128 ± 4 | 41%-50% |
| 10 | SEQ ID NO: 46 | 25 ± 2 | 32 ± 2 | 61%-73% |
| 11 | SEQ ID NO: 47 | 16 ± 2 | 69 ± 4 | 75%-87% |
| 12 | SEQ ID NO: 48 | 40 ± 4 | 138 ± 4 | 38%-46% |
| 13 | Virus group | 64 | 256 | 0 |
| 14 | Negative control group | 0 | 0 | 0 |
| 15 | Normal cell control group | 0 | 0 | 0 |

The above cell-virus experiment results showed that, antisense nucleic acids of SEQ ID NO: 13-24 and peptide nucleic acids of SEQ ID NO: 37-48 all had anti-H3N2 activities; wherein SEQ ID NO: 15, SEQ ID NO: 16, SEQ ID NO: 17, SEQ ID NO: 20, SEQ ID NO: 22, SEQ ID NO: 23 exhibited stronger anti-H3N2 activities.

Preferable sequences selected were mixed by equal mass ratio, and then the anti-H3N2 effect of the mixture was detected. Results showed that, the hemagglutination titer in 36 h was 20±2, and that in 72 h was 36±2. The virus inhibition was 75%-88%.

Toxicity Analysis

Day 1:

Inoculation: early prepared MDCK cells were digested, centrifuged, counted, regulated to $1 \times 10^5$/ml with complete medium and inoculated onto 24-well plates, and then cultured in a 37° C., carbon dioxide chamber for 18-24 hours.

Day 2:

Cell density was observed by microscope till cells grew up to 70~80% of plate area in good condition. Culture solution was removed and 300 µl of drug was added into every well to be selected, 10 wells for each drug, and then cultured again in a 37° C., 5% carbon dioxide environment. A negative control group with PBS only and without peptide nucleic acid was set during the experiment.

Day 3-5:

Toxic effect of drugs against cells was observed and results were evaluated, as shown in Tables 5-8.

TABLE 5

Toxicity analysis on anti-influenza antisense nucleic acids

| NOs | Treatment Antisense nucleic acids | Pathological change of MDCK cell (%) Drug group | Pathological change of MDCK cell (%) PBS |
|---|---|---|---|
| 1 | SEQ ID NO: 1 | 0 | 0 |
| 2 | SEQ ID NO: 2 | 0 | 0 |
| 3 | SEQ ID NO: 3 | 0 | 0 |
| 4 | SEQ ID NO: 4 | 0 | 0 |
| 5 | SEQ ID NO: 5 | 0 | 0 |
| 6 | SEQ ID NO: 6 | 0 | 0 |
| 7 | SEQ ID NO: 7 | 0 | 0 |
| 8 | SEQ ID NO: 8 | 0 | 0 |
| 9 | SEQ ID NO: 9 | 0 | 0 |

TABLE 5-continued

Toxicity analysis on anti-influenza antisense nucleic acids

| NOs | Treatment Antisense nucleic acids | Pathological change of MDCK cell (%) | |
|---|---|---|---|
| | | Drug group | PBS |
| 10 | SEQ ID NO: 10 | 0 | 0 |
| 11 | SEQ ID NO: 11 | 0 | 0 |
| 12 | SEQ ID NO: 12 | 0 | 0 |
| 13 | Normal cell group | 0 | 0 |

Results showed that antisense nucleic acids for H1N1 exhibited no toxicity.

TABLE 6

Toxicity analysis on anti-influenza antisense peptide nucleic acids

| NOs | Treatment Antisense peptide nucleic acids | Pathological change of MDCK cell (%) | |
|---|---|---|---|
| | | Drug group | PBS |
| 1 | SEQ ID NO: 25 | 0 | 0 |
| 2 | SEQ ID NO: 26 | 0 | 0 |
| 3 | SEQ ID NO: 27 | 0 | 0 |
| 4 | SEQ ID NO: 28 | 0 | 0 |
| 5 | SEQ ID NO: 29 | 0 | 0 |
| 6 | SEQ ID NO: 30 | 0 | 0 |
| 7 | SEQ ID NO: 31 | 0 | 0 |
| 8 | SEQ ID NO: 32 | 0 | 0 |
| 9 | SEQ ID NO: 33 | 0 | 0 |
| 10 | SEQ ID NO: 34 | 0 | 0 |
| 11 | SEQ ID NO: 35 | 0 | 0 |
| 12 | SEQ ID NO: 36 | 0 | 0 |
| 13 | Normal cell group | 0 | 0 |

Results showed that antisense peptide nucleic acids for H1N1 exhibited no toxicity.

TABLE 7

Toxicity analysis on anti-influenza antisense nucleic acids

| NOs | Treatment Antisense nucleic acids | Pathological change of MDCK cell (%) | |
|---|---|---|---|
| | | Drug group | PBS |
| 1 | SEQ ID NO: 13 | 0 | 0 |
| 2 | SEQ ID NO: 14 | 0 | 0 |
| 3 | SEQ ID NO: 15 | 0 | 0 |
| 4 | SEQ ID NO: 16 | 0 | 0 |
| 5 | SEQ ID NO: 17 | 0 | 0 |
| 6 | SEQ ID NO: 18 | 0 | 0 |
| 7 | SEQ ID NO: 19 | 0 | 0 |
| 8 | SEQ ID NO: 20 | 0 | 0 |
| 9 | SEQ ID NO: 21 | 0 | 0 |
| 10 | SEQ ID NO: 22 | 0 | 0 |
| 11 | SEQ ID NO: 23 | 0 | 0 |
| 12 | SEQ ID NO: 24 | 0 | 0 |
| 13 | Normal cell group | 0 | 0 |

Results showed that antisense nucleic acids for H3N2 exhibited no toxicity.

TABLE 8

Toxicity analysis on anti-influenza antisense peptide nucleic acids

| NOs | Treatment Antisense peptide nucleic acids | Pathological change of MDCK cell (%) | |
|---|---|---|---|
| | | Drug group | PBS |
| 1 | SEQ ID NO: 37 | 0 | 0 |
| 2 | SEQ ID NO: 38 | 0 | 0 |
| 3 | SEQ ID NO: 39 | 0 | 0 |
| 4 | SEQ ID NO: 40 | 0 | 0 |
| 5 | SEQ ID NO: 41 | 0 | 0 |
| 6 | SEQ ID NO: 42 | 0 | 0 |
| 7 | SEQ ID NO: 43 | 0 | 0 |
| 8 | SEQ ID NO: 44 | 0 | 0 |
| 9 | SEQ ID NO: 45 | 0 | 0 |
| 10 | SEQ ID NO: 46 | 0 | 0 |
| 11 | SEQ ID NO: 47 | 0 | 0 |
| 12 | SEQ ID NO: 48 | 0 | 0 |
| 13 | Normal cell group | 0 | 0 |

Results showed that antisense peptide nucleic acids for H3N2 exhibited no toxicity.

Peptide nucleic acid preparations may be prepared by mixing SEQ ID NO: 25, 29, 30 or 36 and SEQ ID NO: 39, 40, 41, 44, 46 or 47 in a certain mass ratio.

Stability assay on peptide nucleic acid preparations

High temperature: the bioactivity was not affected by sterilization on high temperature of 105° C. in steam circulation for 20 minutes.

Extreme temperature: the bioactivity was not affected by storage at 50° C. for 2 months.

Room temperature: the bioactivity was not affected by storage for 24 months.

Low temperature: the bioactivity was not affected by storage at −20° C. for 48 months.

What is claimed:

1. An anti-influenza virus H1N1 antisense peptide nucleic acid, characterized in that it is selected from any one or more of the following sequences:

```
SEQ ID NO: 26:    5'-AATGTTATCTCCCTCTTAAGCTT-3';
SEQ ID NO: 27:    5'-CATGTCTTATTAATGGATTAGTT-3';
SEQ ID NO: 28:    5'-CGATCAATAATCCACAATATCAG-3';
SEQ ID NO: 31:    5'-TCTTACTTGATCCATCATTGCCC-3;
SEQ ID NO: 32:    5'-ACATTCTCATTTGAAGCAATCTG-3';
SEQ ID NO: 33:    5'-CGTCTTCTTTCTTCTCTTTTGTT-3';
SEQ ID NO: 34:    5'-TCTTCTTACTATGTTTCTAGCAG-3';
SEQ ID NO: 35:    5'-CAATTATTGCCTCAGCAATTGAC-3';
SEQ ID NO: 36:    5'-GAACTGTAAGTCGTTTGGTTGCC-3.
```

2. The antisense peptide nucleic acid of claim 1, characterized in that the sequence is:
SEQ ID NO: 36: 5'-GAACTGTAAGTCGTTTGGTTGCC-3.

3. An anti-influenza H3N2 antisense peptide nucleic acid, characterized in that it is selected from any one or more of the following sequences:

```
SEQ ID NO: 37:    5'-TTGTATATGAGGCCCATGCAACTGG-3';
SEQ ID NO: 38:    5'-TGATCCAGCCATTTGCTCCATAGCC-3';
SEQ ID NO: 42:    5'-ACTTTCTCTCACTTGATCCAC-3';
SEQ ID NO: 43:    5'-CCATCGACTCTCCTGTATATGG-3';
SEQ ID NO: 44:    5'-TCATTCTTATGATTTCTGCCC-3';
SEQ ID NO: 45:    5'-TGGTTTTTGTCAGTATCTCGC-3';
SEQ ID NO: 46:    5'-TCCTATTCCACCATGTTACAG-3';
SEQ ID NO: 47:    5'-ATTGTTAATTGTGATTCTGAT-3';
SEQ ID NO: 48:    5'-GAGTTGAACCAATCTTCTGGTTG-3'.
```

4. The antisense peptide nucleic acid of claim 3, characterized in that it is selected from any one or more of the following sequences:

```
SEQ ID NO: 44:    5'-TCATTCTTATGATTTCTGCCC-3';
SEQ ID NO: 46:    5'-TCCTATTCCACCATGTTACAG-3';
SEQ ID NO: 47:    5'-ATTGTTAATTGTGATTCTGAT-3'.
```

5. The antisense peptide nucleic acid of claim 1, characterized in that it may further be prepared into an antisense peptide nucleic acid preparation by adding pharmaceutically acceptable carriers or excipients.

6. The antisense peptide nucleic acid of claim 2, characterized in that it may further be prepared into an antisense peptide nucleic acid preparation by adding pharmaceutically acceptable carriers or excipients.

7. The antisense peptide nucleic acid of claim 3, characterized in that it may further be prepared into an antisense peptide nucleic acid preparation by adding pharmaceutically acceptable carriers or excipients.

8. The antisense peptide nucleic acid of claim 4, characterized in that it may further be prepared into an antisense peptide nucleic acid preparation by adding pharmaceutically acceptable carriers or excipients.

* * * * *